(12) United States Patent
Mikosz et al.

(10) Patent No.: US 12,102,750 B2
(45) Date of Patent: Oct. 1, 2024

(54) METHOD AND DEVICE FOR MONITORING DRUG INTAKE

(71) Applicant: FINDAIR SP. Z O. O., Cracow (PL)

(72) Inventors: Tomasz Mikosz, Michalowice (PL); Jacek Mikosz, Cracow (PL); Michal Czyz, Cracow (PL)

(73) Assignee: FINDAIR SP. Z O. O., Cracow (PL)

( * ) Notice: Subject to any disclaimer, the term of this patent is extended or adjusted under 35 U.S.C. 154(b) by 716 days.

(21) Appl. No.: 17/280,195

(22) PCT Filed: Sep. 26, 2019

(86) PCT No.: PCT/PL2019/050054
§ 371 (c)(1),
(2) Date: Mar. 26, 2021

(87) PCT Pub. No.: WO2020/167146
PCT Pub. Date: Aug. 20, 2020

(65) Prior Publication Data
US 2021/0346618 A1    Nov. 11, 2021

(30) Foreign Application Priority Data

Sep. 27, 2018   (PL) .......................................... 427235

(51) Int. Cl.
*A61M 15/00*   (2006.01)
(52) U.S. Cl.
CPC ...... *A61M 15/008* (2014.02); *A61M 15/0025* (2014.02); *A61M 15/009* (2013.01);
(Continued)

(58) Field of Classification Search
CPC ...... A61M 11/00; A61M 11/04; A61M 11/06; A61M 11/08; A61M 15/00;
(Continued)

(56) References Cited

U.S. PATENT DOCUMENTS

| 5,363,842 A | 11/1994 | Mishelevich et al. |
| 5,505,192 A | 4/1996 | Samiotes et al. |

(Continued)

FOREIGN PATENT DOCUMENTS

| EP | 0752895 B1 * | 7/1998 |
| EP | 1726322 A1 | 11/2006 |

OTHER PUBLICATIONS

Extended European Search Report for EP Application No. 19915559.9 Mailed on Mar. 18, 2022.

*Primary Examiner* — Rachel T Sippel
(74) *Attorney, Agent, or Firm* — Rivka Friedman

(57) ABSTRACT

A device for monitoring drug use from a drug dispenser in the form of a dispenser cap, especially an inhaler, comprising a sensor for measuring drug release from the dispenser. As a drug release measurement sensor (2) a piezoelectric transducer (2) is used, while a piezoelectric transducer (2) is connected to a microprocessor. The cap includes the activator (1) of the drug release measurement sensor (2) associated movably connected with the piezoelectric transducer (2), wherein the piezoelectric transducer (2) is located in the cap in such a way that, with the help of the activator (1) of the drug release measurement sensor (2), after using the drug dispenser, the force pressure on the cap as a kinetic force is transmitted from the activator (1) of the drug release measurement sensor (2) directly to the piezoelectric transducer (2), which measures the transferred kinetic force.

12 Claims, 8 Drawing Sheets

(52) U.S. Cl.
CPC ............... *A61M 2205/0211* (2013.01); *A61M 2205/0216* (2013.01); *A61M 2205/332* (2013.01); *A61M 2205/3375* (2013.01); *A61M 2205/50* (2013.01); *A61M 2205/581* (2013.01); *A61M 2205/8206* (2013.01)

(58) Field of Classification Search
CPC .......... A61M 15/0001; A61M 15/0065; A61M 15/0068; A61M 15/008; A61M 2205/332; A61M 2205/3375; A61M 2205/581
See application file for complete search history.

(56) References Cited

U.S. PATENT DOCUMENTS

| | | | |
|---|---|---|---|
| 2005/0011515 A1* | 1/2005 | Lee | A61M 15/0091 128/200.23 |
| 2009/0229607 A1 | 9/2009 | Brunnberg et al. | |
| 2011/0041845 A1* | 2/2011 | Solomon | A61M 15/009 128/203.12 |
| 2015/0235548 A1 | 8/2015 | Engelhard | |
| 2016/0144141 A1* | 5/2016 | Biswas | A61M 15/009 128/200.23 |
| 2017/0348496 A1* | 12/2017 | Leane | G01L 1/16 |
| 2018/0326164 A1* | 11/2018 | Bauss | A61M 5/20 |

\* cited by examiner

METHOD AND DEVICE FOR MONITORING DRUG INTAKE

The invention refers to a method and device for monitoring drug, medicines, intake—detecting and signaling drug use from a dispenser, and in particular for monitoring of drug use from an inhaler.

Monitoring administration of a dispenser is important because of the need to control and comply with the therapeutic regimen. Drug intake monitoring also helps to correctly diagnose and determine the effective therapeutic dose. Various types of drugs—pharmaceuticals, medicines—are known, which can be in the form of liquids, powders, tablets or suspensions. In description drug means medicine.

Intake of some medications may require a special dispenser to deliver them, by which the specific dose of the drug is released. These dispensers can be in the form of containers or various types of inhalers.

In particular, monitoring drug use is important when introducing a strong drug.

Some drugs are delivered in the form of a dispersed spray. Most often in this way some amount of drugs are administered to the respiratory tract, i.e. by oral inhalation, or by applying on the skin. Devices for generating an aerosol and administering a dose of a drug substance in the form of an aerosol by inhalation are inhalers or nebulizers that contain compressed air to disperse the pharmaceutical dose. There are pressure and powder inhalers, as well as pneumatic and ultrasonic nebulizers.

Currently, the most commonly used inhaler in the treatment of allergic diseases is the pMDI inhaler—pressurized Metered Dose Inhaler, i.e. a pressure inhaler with a dispenser. It is widely used in the treatment of upper respiratory tract diseases. The general structure of the known inhaler is shown in FIG. 1.

As shown in FIG. 1, the administration of the drug from the inhaler is based on the principle that the user presses the upper movable proper part of the dispenser B with the kinetic force T, supporting the lower part of the actuator A. The actuator is an element of the inhaler design that allows the drug dispenser to be mounted in inhaler as well as directional release of the drug from the dispenser. Directional release of the drug from the dispenser B using actuator A is possible by mounting the dispenser B in actuator A and in particular by resting the dispensing valve in dispenser B against the directional nozzle in actuator A. Pressing with kinetic force T on the drug dispenser B causes the dispenser B dispensing valve to rest against the directional nozzle of the actuator A, and then the dispenser B dispensing valve slides into the dispenser B. During this process, a single metered dose of formulation is released that contains the drug dissolved or suspended in the propellant. Breaking the volatile propellant into droplets and then rapidly evaporating these droplets produces an aerosol containing micrometer-sized particles, which are then inhaled.

Due to the construction of pMDI inhalers, they release a measured dose of the drug only when the upper part of the drug dispenser is pressed with adequate kinetic force such that the movement of the upper part of the dispenser caused by pressing leads to the complete depressing of the dosing valve in the drug dispenser. Depending on the structure and design of the dispensing valve in dispensers, inhalers may differ from each other by the minimum level of kinetic force T that is required to release the drug through the dispensing valve in the dispenser B. The minimum level of kinetic force T required to release the drug depends on the mechanical resistance of the metering valve in the dispenser B. It follows that not every press on the container will release the medicine from it. Pressing may have insufficient kinetic force, as a result of which the metering valve in the dispenser B will not be fully depressed and the propellant containing the drug will not be released.

Solutions for controlling drug use which are used with pMDI inhalers are known. An example of such solution are caps for the inhaler—in a form of extension for dispenser The solution for measuring the release of the administered dose of the drug from the pMDI inhaler in the form of a cap C attached to the upper part of the dispenser is shown in FIG. 2. In this case, the release of the drug from the dispenser does not occur as a result of direct pressing of the drug dispenser with adequate kinetic force and as a result of pressing the kinetic force $W1$ on the cap C, which is mounted on the dispenser B with the drug. As a result of pressing the cap C with the kinetic force $W1$, some of the kinetic force $W1$ pressing on the cap can be converted into a spring force by deforming some elements of the cap C. The resulting, reduced kinetic force $W2$ of the pressure is transferred to the upper part of the drug dispenser B leads to full depressing of the metering valve in dispenser B with the drug. The value of the kinetic force $W1$ with which the top of the cap is pressed and the value of the kinetic force $W2$ with which the drug dispenser is pressed are an important condition determining whether the drug has been released.

Various types of sensors for measuring drug release from a dispenser are known and used in dispensers—inhalers and caps for its. Known sensors record drug release from the dispenser during pressing an electronic button. The electronic button in order to be able to record the release of the drug contains a built-in resilient plate or breakout spring, which must be bent to allow the system to short-circuit—to pass an electrical impulse, recorded by the microprocessor as the use of the drug—release of the drug. As a result, threshold of the required kinetic force—mechanical resistance is fixed in the button, for the electronic button activation and can operate only on a zero-one rule. The button is mounted on the electronic module in such a way that it can absorb the kinetic force $W1$ as a result of the pressure on the cap. In the event of pressure on the cap, the kinetic force $W1$ coaxial to the dispensing valve in the drug dispenser and whose value during being pressed will be higher or equal to the mechanical resistance of the electronic button, the system short circuits and the electronic button begins to conduct current. This situation is interpreted by the microprocessor as intake of the drug. In the event of pressure by the kinetic force on the pad, in which the value when pressed will be lower than the mechanical resistance of the electronic button, there is no short circuit of the system, so there is no current conduction and this situation is not recorded by the microprocessor.

Caps in the form of an electronic button to detect the application of kinetic force on a cap are known. In particular, the patent applications U.S. Pat. Nos. 5,505,192A, 5,622, 163 describe an element detecting the application of the kinetic force on the cap is an electronic button, which when pressed causes a short circuit and begins to conduct current. This is interpreted by the microprocessor as taking the medicine.

In known inventions in the form of caps and inhalers there are numerous problems and limitations resulting from the use of the electronic button as a drug release sensor from the dispenser.

As a result of using the electronic button in the caps and inhalers as the drug release sensor from the dispenser, which allows measuring the exceeding of the required kinetic force threshold on a zero-one basis, it is not possible to record the exact value of the kinetic force with which the dosing valve was pressed in the drug dispenser. This restriction is called "zero-one counting".

Another limitation resulting from the problem of "zero-one counting" is the inability to register drug use attempts—incorrect use of the drug. It is not possible to register the kinetic force of the pressure on the drug dispenser whose W2 value was below the threshold of the required kinetic force of pressure on the drug dispenser to release the drug. This restriction is called "no invalid operation".

Known inventions also do not have the possibility of using the same variant of the cap with an electric button for different inhalers and drug dispensers, with different thresholds of the required pressure force resulting from the mechanical resistance of the dispensing valve. The need to use a dedicated version of the cap using the electronic button results in, when trying to manufacture, fragmentation of production for different versions of the cap for different inhalers and drug dispensers, as well as the inability of the user to adapt the cap to changing inhalers and dispensers during the treatment process. This limit is called the "cap dedicated to the inhaler."

Another important aspect of conducting therapy is the possibility of informing the patient about various types of events related to the condition of the device, with an attempt to take the drug or with the various stages of the attempt to take the drug. For this purpose, various devices using sound signalling are used. An example of such events may be events related to the use of the drug, e.g. signalling the moment of counting the consumption of the drug by the cap, signalling the moment of pressing the cap, signalling the moment of the end of pressing the cap, signalling the correctness of the entire drug administration process—correct drug consumption, signalling the occurrence of a problem during taking the drug—attempt to take the drug, continuous signalling during the suggested time of inhaling the drug from the inhaler, etc.

One of the solutions used in inhalers for audible signalling of events related to the use of the drug are loudspeakers or piezoelectric transducers.

Piezoelectric material is characterized by the fact that during mechanical stress it generates electric charges. The reverse phenomenon also occurs, which changes the shape of the material when an electric charge is delivered to it (thanks to which it can produce sound waves).

Known piezoelectric transducers are shown in FIG. 3. As shown in FIG. 3, known piezoelectric transducers comprise two metal claddings X, between which is a thin layer of ceramic material having piezoelectric properties Y.

There are known solutions enabling communication of a drug recording device with a patient by means of sound. From the description of the invention U.S. Pat. No. 5,363,842 it is known to use a piezoelectric transducer in inhalers as a generator for signalling the administration of a drug, which is registered using an electronic button. In this solution, the electronic button is located on the bottom of the actuator housing. Its task is to register the use of the inhaler by detecting the kinetic force applied to the drug dispenser. The piezoelectric transducer is mounted in the front of the actuator. The task of this element is sound signalling of various events related to the condition of the device, the correct use of medication, an attempt to take the medication or with the various stages of medication. The piezoelectric transducer and the electronic button are not functionally related to each other, one element—the piezo transducer is used for sound signalling, while the other electronic button is used for recording use. According to the invention, these elements must be detachable, the electronic button at the bottom of the actuator, and the piezoelectric transducer in the front of the actuator. These are places that are not adjacent, which significantly complicates the construction of this device. In the cited example, by using the electronic button as the element detecting pressure on the inhaler, the fact of pressure is measured only on a zero-one basis. This is due to the designed, constant threshold of the required pressure force of the electronic button. Its ability to accurately measure pressure is not provided for in this solution. In contrast, the piezoelectric transducer in the cited example is used only as a sound generator signalling about events recorded by an electronic button. The invention presented in U.S. Pat. No. 5,363,842 patent provides for the use of these two different elements in the device in the form of an actuator, i.e. a feeder, matching the drug container, which is necessary part of the drug release system. However, it is not possible to design such a device in the form of an inhaler cap independent of the actuator.

The solution described in patent EP0752895 is known, which uses a piezoelectric transducer as a sensor—pressure sensor in the cap on the drug dispenser. To determine the amount of medicine remaining in the drug dispenser. The cap using the pressure sensor on the dispenser using a microprocessor records the number of sensor presses during drug administration, which are then compared with the initial number of doses in the dispenser, allowing the amount of drug remaining in the dispenser to be calculated. This solution is not used to dynamically measure the kinetic force of the pressure on the piezoelectric transducer to determine if the kinetic force of the pressure was sufficient to release the drug from the drug dispenser, but only to record the number of pressures of the cap mounted on the dispenser. This limitation also results from the use of a spring element in this solution between the piezoelectric transducer and the drug dispenser which converts part of the kinetic force of the pressure into the elastic force of the spring element, as a result the kinetic force of the pressure acting on the piezoelectric transducer is not equal to the kinetic force of the pressure on the drug dispenser, which prevents direct measurement of the kinetic force of the pressure on the dispenser based on the value of the kinetic force of the pressure acting on the piezoelectric transducer, which makes it impossible to determine whether the user was acting with a kinetic force of pressure sufficient to properly release the drug from the dispenser. This solution also does not provide for the possibility of connecting the sensor with other external devices via wireless communication.

According to the invention, a piezoelectric transducer is used as the drug release measurement sensor. The piezoelectric transducer is mounted in the cap and positioned so that, when applied to the cap kinetic force, the kinetic force is transferred through an movable element of the cap—activator for the drug release measurement sensor—the piezoelectric transducer—directly to the piezoelectric transducer located coaxially to the drug release measurement sensor activator—a piezoelectric sensor—that is, a movable element that directly transmits the kinetic force made when the pressure on the cap. This design of the cap according to the invention allows the use of a piezoelectric transducer both as a measure of the kinetic force of the pressure on the drug dispenser in the inhaler to register the use of the drug dispenser, especially the inhaler, and especially to monitor the use of the drug, understood as the release of the drug from the inhaler and its consumption by the user at the recommended dose, as well as an additional audible signalling device for various events related to the use of the inhaler, including signalling of correct or incorrect use, signalling of individual stages when attempting to use the inhaler, i.e. the stage of exhalation of air from the lungs before the release of the inhaler, the stage of using the inhaler and inhaling the drug, the stage of holding the drug in the respiratory system breathing after the end of inhalation of the drug, and signalling of events related to the device status, i.e. high and low battery level in the device, starting and ending the connection of the device with a mobile device, device connection failure with mobile device.

According to the invention, the piezoelectric transducer is located in the cap coaxially to the activator of the drug release measurement sensor—of the piezoelectric sensor—i.e. a movable element that directly transmits kinetic force when pressure is applied to the cap on the piezoelectric transducer. In this way, the piezoelectric transducer—drug release measurement sensor, is a measure of the magnitude of the kinetic force applied to the drug dispenser, regardless of whether the drug is properly released from the dispenser or regardless of whether the drug dose is released correctly—attempting to release the dose. This enables the kinetic force to be accurately measured on the piezoelectric sensor transducer and thus on the drug dispenser during the pressure on the cap to induce drug delivery from the inhaler. The activator of the drug release measurement sensor—piezoelectric sensor—can be made as a single element or as a design of many elements, enabling the absorption of kinetic force resulting from the pressure on the cap. Activator elements can be made of materials such as metals, polymers, ceramics, composites, elastomers.

The piezoelectric sensor activator is connected to the piezoelectric sensor by means of a kinetic force intermediary between the kinetic force source acting on the cap and the piezoelectric sensor in such a way that the activator allows the kinetic force to be transferred to the piezoelectric sensor. The activator is an additional element protecting against damage to the piezoelectric sensor in case it is directly on the top of the cap.

Inhalers to activate them, through the metering valve in inhalers, require pressure on a drug dispenser with a specific kinetic force to allow the dispensing valve of the drug dispenser to be inserted into the drug dispenser. Although inhalers from different manufacturers may have different required kinetic strength to activate them, it is always the minimum required kinetic force of pressure that causes the release of a single, metered dose of the drug or the start of drug release. Thanks to the construction of the cap according to the invention, it is possible to recognize the kinetic force of the pressure with which the piezoelectric transducer is pressed, and thus to recognize whether there was sufficient kinetic force of the pressure sufficient for the proper release of the drug, regardless of the threshold of the required kinetic force of pressure that causes the release of the drug in individual inhalers of different manufacturers. Therefore, it is possible to distinguish the following events by means of the invention: whether the cap was pressed, what kinetic force was acting on the piezoelectric transducer when the cap was pressed, whether the kinetic force with which the piezoelectric transducer was pressed was sufficient to release the dose of the drug in accordance with the manufacturer's requirements, how many times the cap was pressed. The invention also has the ability to determine and record cases of pressing the cap with a kinetic force that will be too low to release a dose of the drug from the inhaler.

According to the invention, it is also possible to use the same piezoelectric transducer to generate audible signals that are intended to signal various events related to the use of the dispenser, especially the inhaler, drug release or its use, including signalling the correct or incorrect use of the dispenser, signalling individual stages during attempts to use the inhaler and signalling events related to the device status. Using instead of two elements: an electronic button and a piezoelectric transducer, one element, which is a piezoelectric transducer, for two purposes, reduces the complexity of the device and allows reducing its size, which in turn increases its ergonomics and reduces production costs. The construction of the cap according to the invention also avoids the limitations and problems that occur in known caps using the electronic button as a drug release measurement sensor. In the proposed invention, due to the use of a piezoelectric sensor, which measures a wide range of kinetic force of pressure continuously, it is possible to record the exact value of the kinetic force with which the dispensing valve was pressed in the drug dispenser, so there is no problem of "zero-one counting". Thus, the invention makes it possible to register a situation of incorrect use of a drug—an attempt to use a drug—occurring during the use of insufficient kinetic force on the drug dispenser to release the drug, solving the problem of "no incorrect pressing". Thanks to the ability to measure a wide range of kinetic force continuously, the cap need not be limited to use only with a dedicated inhaler or drug dispenser. By reprogramming the pressure threshold in the microprocessor using wireless devices, it is possible to use the same design variant of the cap for different inhalers and drug dispensers with different thresholds of the required kinetic force of pressure as a result of the mechanical resistance of the dosing valve, as well as the user can adapt the cap to changing inhalers and dispensers in the treatment process, thereby solving the problem of "cap dedicated to the inhaler".

The subject matter of the invention is the specific structure of the inhaler cap, recording the use of the drug and enabling the generation of acoustic signals, using the structure and principle of operation of drug dispensers and the electro-mechanical properties of piezoelectric transducers.

In order for the cap for the inhaler using the piezoelectric transducer to act as a sensor of the kinetic force of pressure on the drug dispenser to release the drug from the dispenser, the piezoelectric transducer used in the cap must be between the place of applying the kinetic force of the pressure on the cap, i.e. the activator of the drug release measurement sensor—sensor piezoelectric—and the drug dispenser and between the piezoelectric transducer and the drug dispenser there are no elastic elements. This design of the device causes, that the kinetic force applied to the cap to activate the dispenser and release the drug, is transferred by the activator to the piezoelectric transducer as well as causes that the value of the kinetic force transferred to the piezoelectric transducer is equal to the value of the kinetic force transferred to the drug dispenser. After the activator transfers the kinetic force applied to the cap and transmits it to the piezoelectric transducer, due to its piezoelectric properties, the piezoelectric transducer converts the kinetic force of the pressure that was applied to it into an electric charge directly proportional to this force. This process results in the release of electrical impulses to the microprocessor. The microprocessor records the received electrical impulses as numerical values, which it compares with the previously programmed required numerical value—pressure threshold. If the electrical impulses resulting from the application of kinetic force to the piezoelectric transducer are greater than the numerical value programmed in the microprocessor—the pressure threshold—then the microprocessor verifies this as the correct use of the drug. If the electrical impulses resulting from the application of the kinetic force to the piezoelectric transducer are smaller than the numerical value previously programmed in the microprocessor—the pressure threshold, then the microprocessor verifies this as incorrect drug use—an attempt to use the drug. The kinetic force applied to the piezoelectric transducer is transmitted to subsequent components of the device up to the housing mounted on the drug dispenser, then on the drug dispenser, which is based on the actuator and as a result the drug is released.

The invention has been described in more detail in the embodiments and in the drawing in which.

Figure 1:
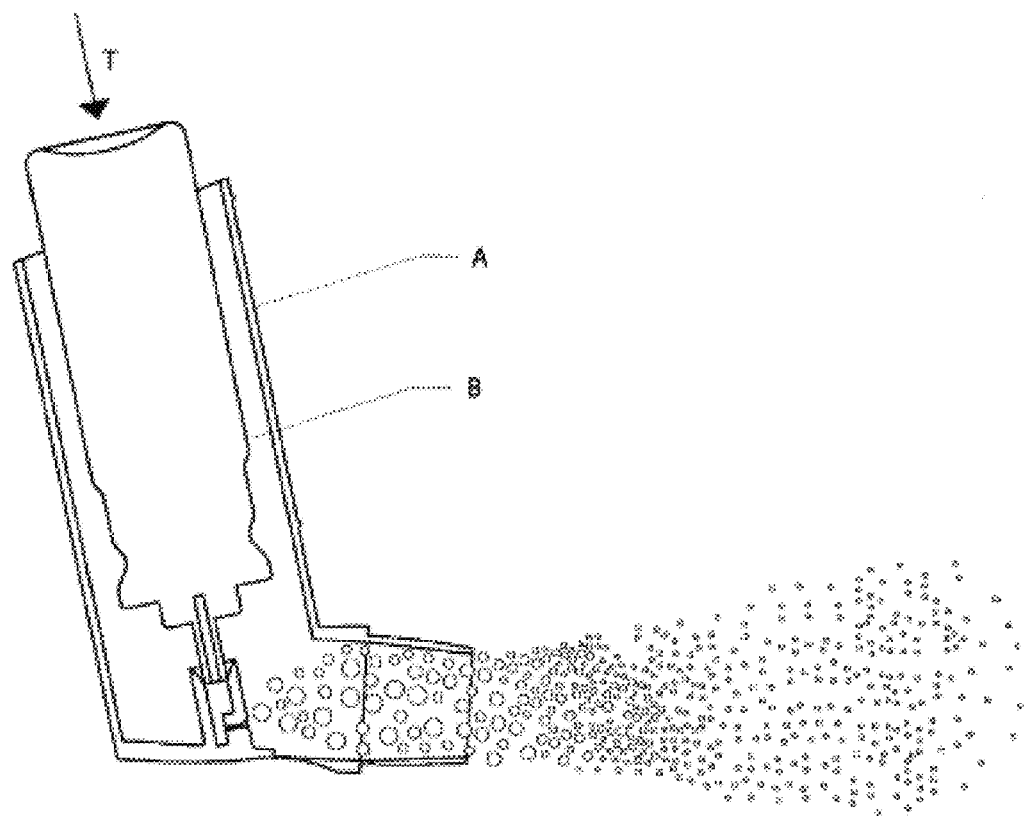
FIG. 1 shows a general structure of the known inhaler.
Figure 2:
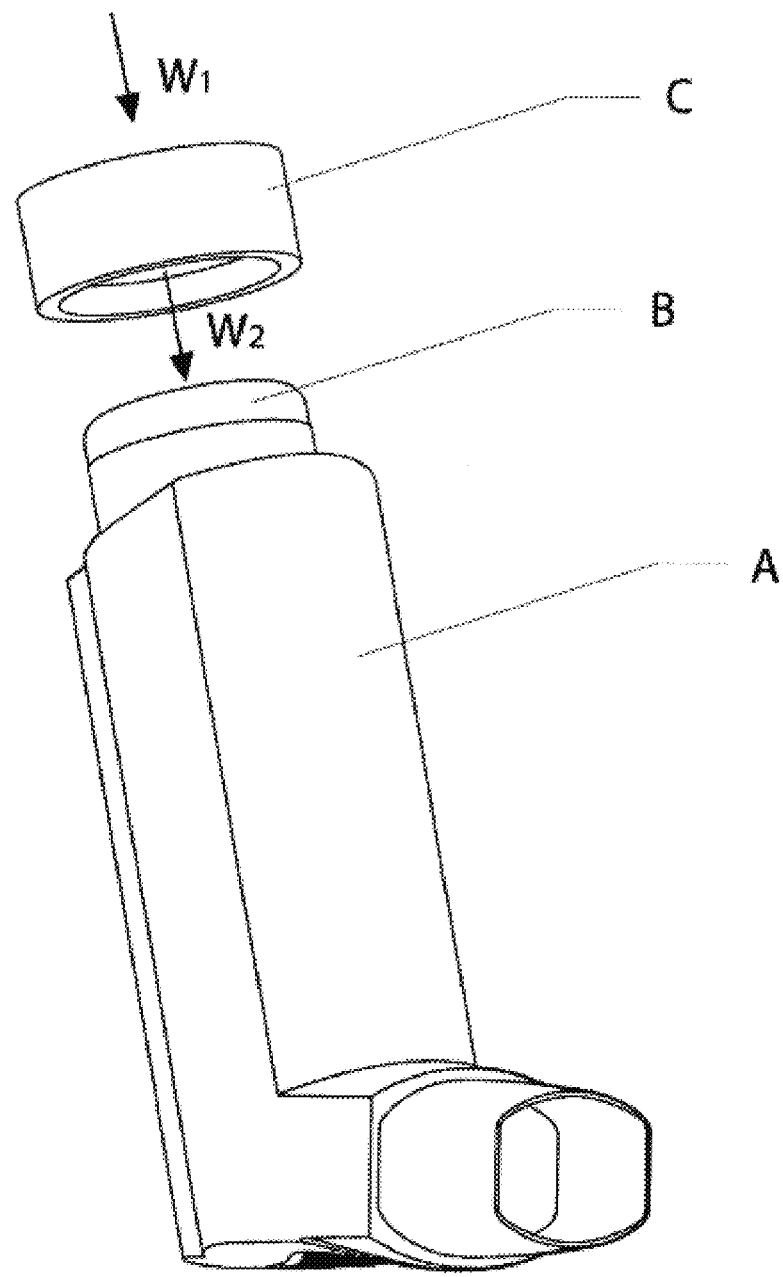
FIG. 2 shows a cap C attached to the upper part of the dispenser.
Figure 3:
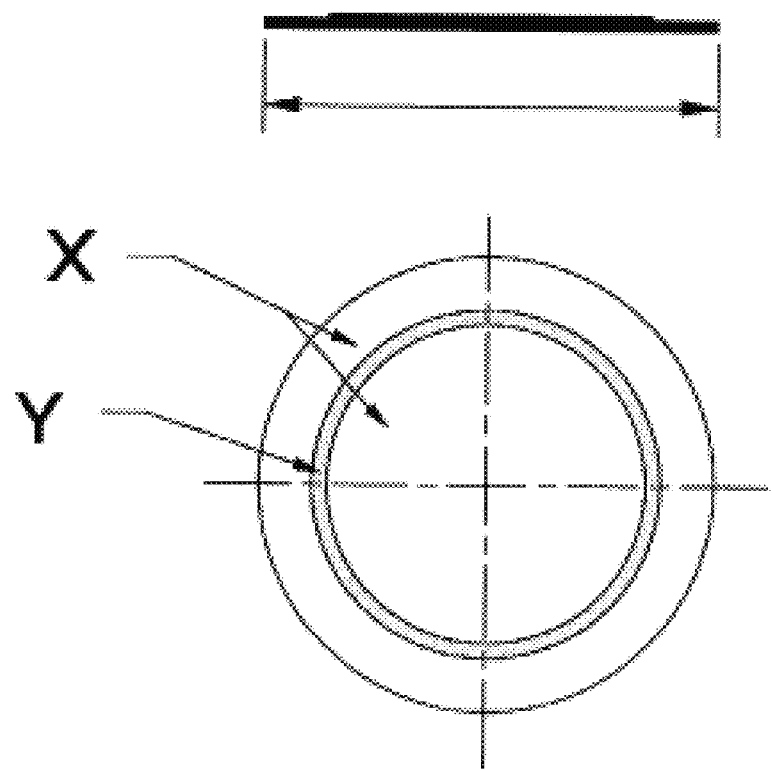
FIG. 3 shows known piezoelectric transducers.
Figure 4:
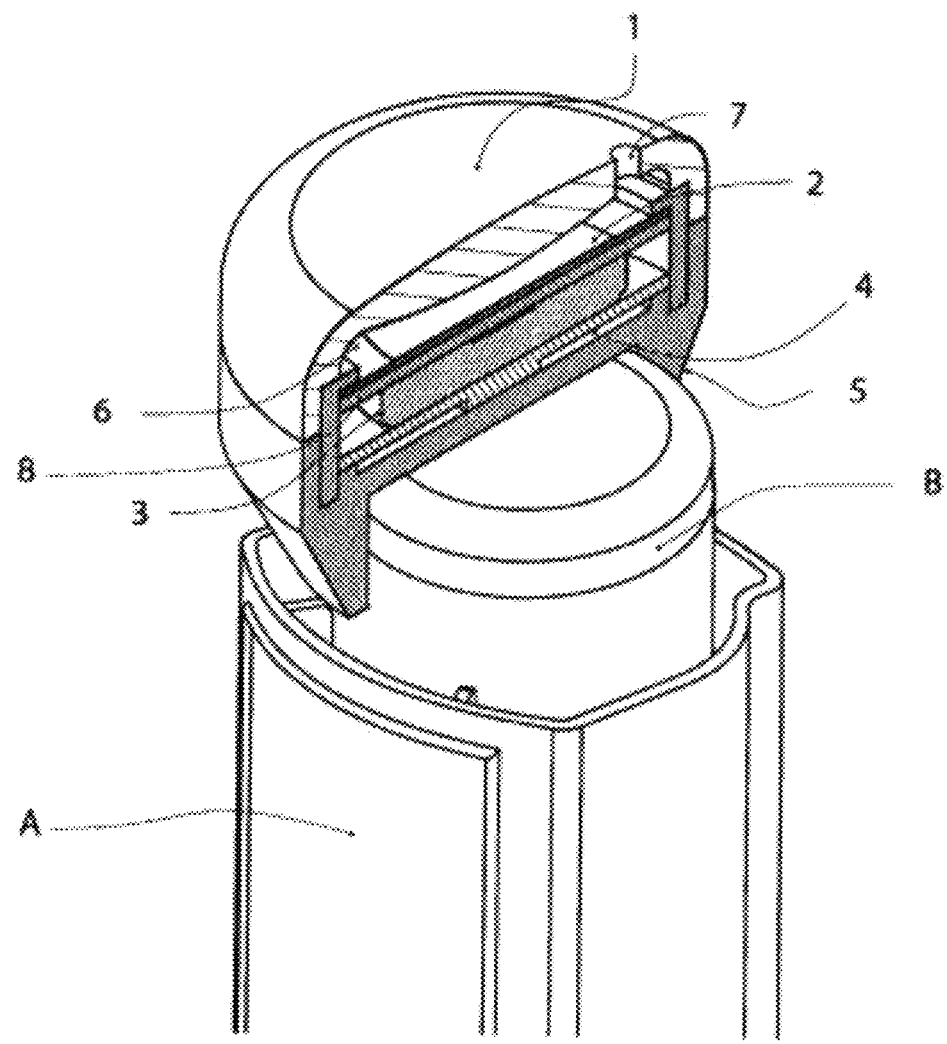
Figure 5:
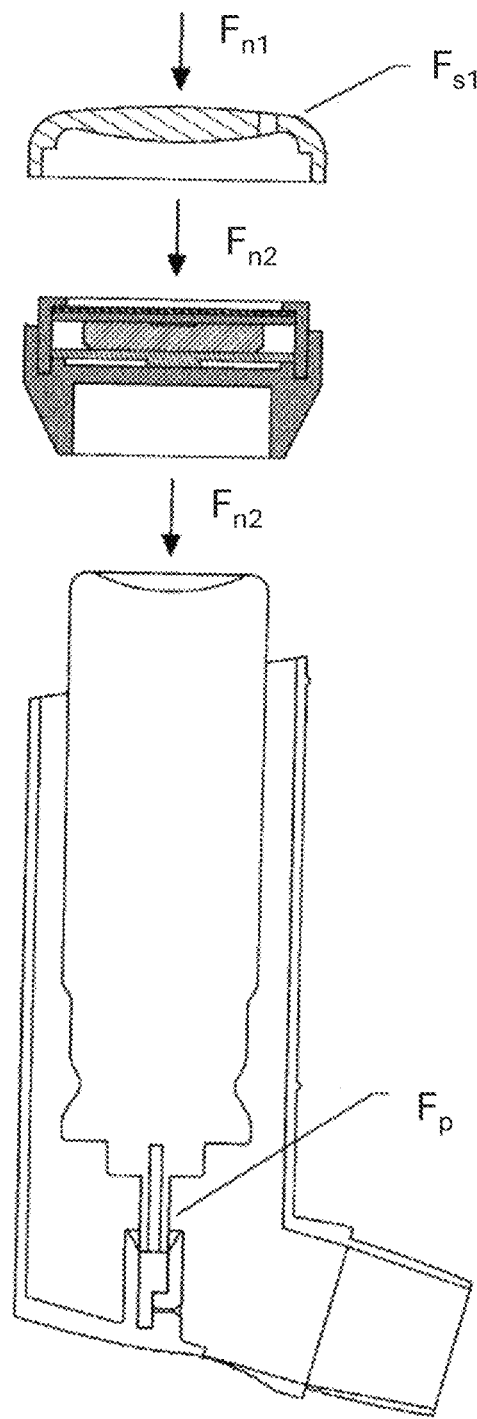
Figure 6:
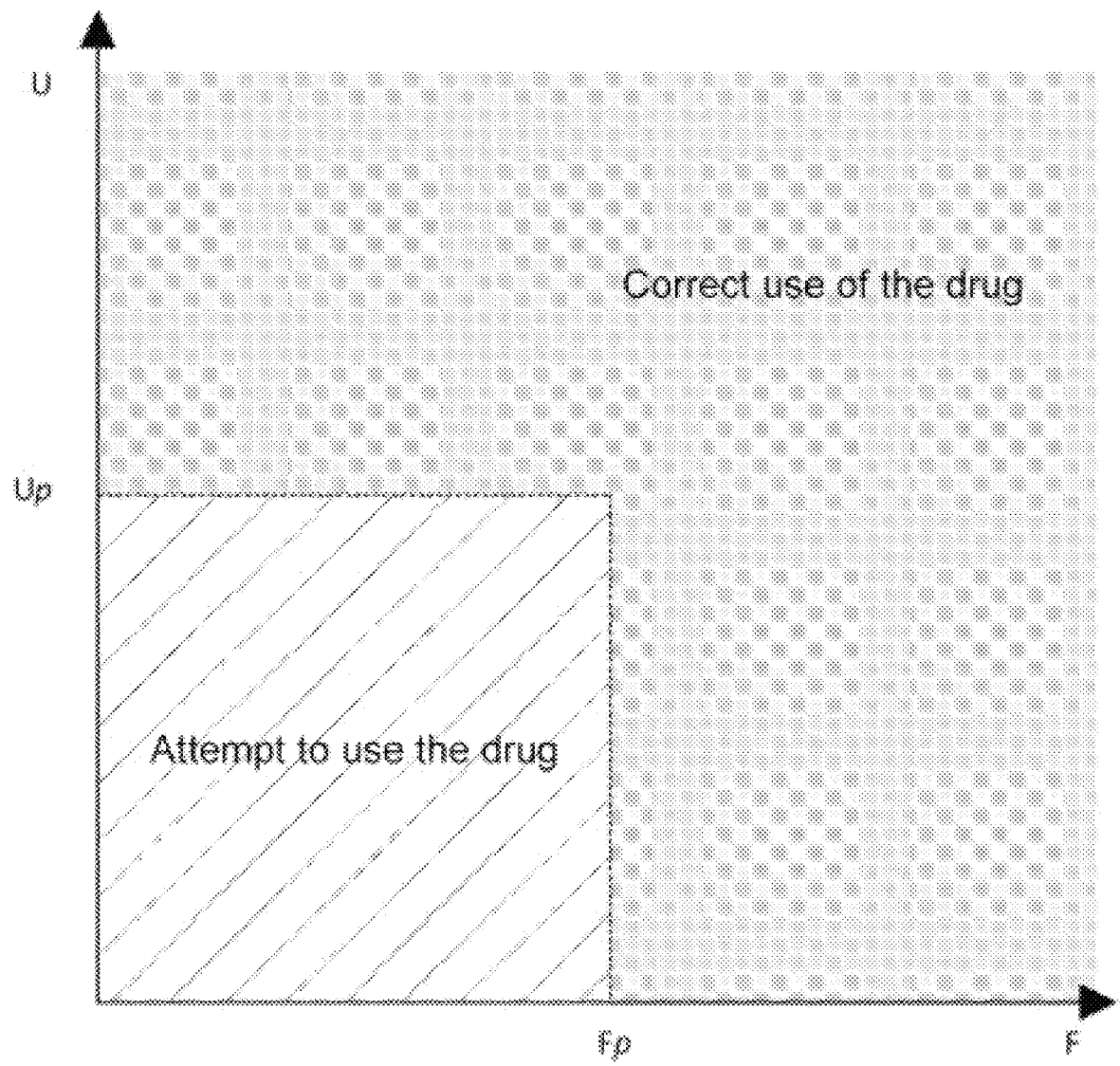

FIG. 4 is a cross-sectional view of the cap of the invention mounted on the drug dispenser in a first embodiment, FIG. 5 is a cross-sectional view of the inhaler and cap according to the invention and together with the kinetic forces of pressure and elastic forces acting on individual elements of the invention in the first embodiment, FIG. 6 shows the principle of the microprocessor verifying the value of the kinetic force of the pressure and the value of the electric voltage as the correct use of the drug or an attempt to use the drug.

Figure 7:
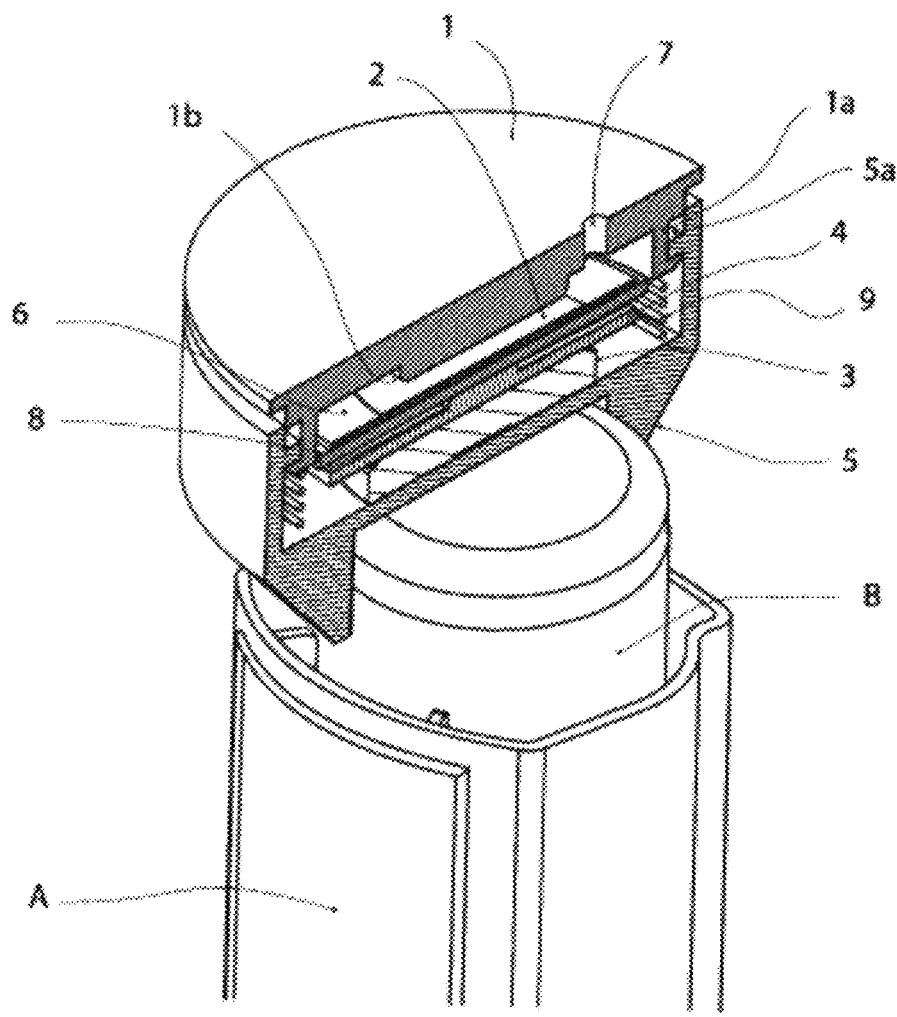
Figure 8:
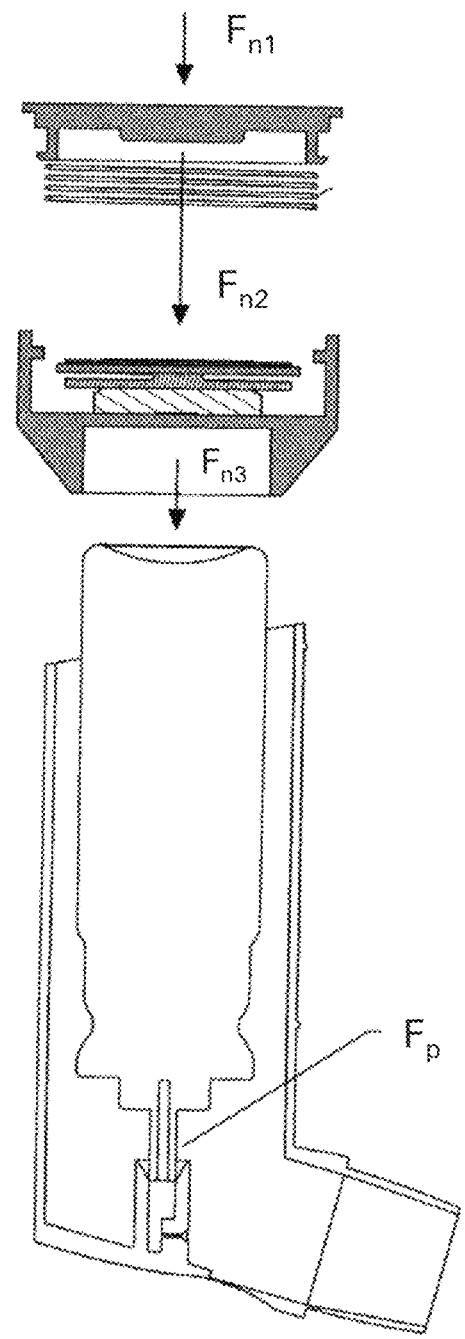

FIG. 7 is a cross-sectional view of the cap of the invention mounted on the drug dispenser in a second embodiment, FIG. 8 shows a cross-sectional view of the inhaler and cap according to the invention and together with the kinetic forces of pressure and elastic forces acting on individual elements of the invention in a second embodiment.

EXAMPLE 1

Construction of the Drug Dispenser Cap

As shown in FIG. 4, the cap includes such elements as:

Activator 1 of the drug release measurement sensor—drug release sensor—a sensor in the form of a piezoelectric transducer—constituting the top cover, piezoelectric transducer 2, isolation plate 8, coin-cell battery 3, electronic module 4 containing a microprocessor, bottom housing 5 with mounting on the dispenser, resonance chamber 6. Upper housing, in order for it to act as an activator of the drug use sensor—piezoelectric transducer—it must be made of a semi-oval elastomer that allows it to be fitted on the bottom housing 5, as well as due to the elasticity of the material from which it is made, allow it to deflect into the resonance chamber 6, as well as to find coaxial to the drug release measurement sensor. An hole 7 is provided in the activator of the drug release measurement sensor—a piezoelectric transducer—positioned in a way that allows the sound from the piezoelectric transducer 2 to spread outside the cap. In description hole means opening.

Construction and Principle of the Invention in Example 1

As shown in FIG. 4, the cap is mounted on the dispenser e.g. on the inhaler on the drug dispenser. The drug dispenser B is inserted into the actuator A equipped with a nozzle for directing the drug out of the inhaler. The cap can be applied to known inhalers or other drug dispensers in such a way that the cap is mounted on the dispenser B, and that the cap is coaxial to the dispensing valve in the dispenser B, and that the cap does not block the release of the drug through the dispenser B, as well as the cap did not block the expulsion of the drug from the inhaler through the nozzle in actuator A. The piezoelectric transducer 2 is located underneath the activator 1 of the drug release measurement sensor—piezoelectric transducer—which is the top cover, with which the dispenser is not in close contact with the base state—it does not adhere to the top cover 1, but between the position of the upper cover 1 and the piezoelectric transducer 2 is the distance equal to the mobility of the upper cover 1, when the drug is released, in relation to the piezoelectric sensor 2.

When the inhaler is not in use, between the piezoelectric transducer 2 and the activator 1 of the piezoelectric transducer, which in its embodiment is the top cover, a free space is created that forms the resonance chamber 6. Activator 1 is made of an elastomer which is able to deform under the influence of pressure applied to it during administration of the medicine. Activator 1 of the drug release measurement sensor—piezoelectric transducer—which is the upper cover, which through movement transmits the pressure force—kinetic force causing movement—deformation of the upper cover—to the piezoelectric sensor, thus causing pressure on the piezoelectric sensor 2 and thus its deformation. The deformation of the piezoelectric transducer absorbs a small amount of kinetic force of the pressure for the invention, so it can be assumed that the kinetic force of the pressure acting on the piezoelectric transducer and the kinetic force of the pressure transmitted to subsequent elements of the device is a kinetic force of the same value. At the moment of pressure on the cap, the activator 1 of the drug release measurement sensor—piezoelectric transducer—which is the top cover deforms by transferring the kinetic force of the pressure on the piezoelectric transducer 2, which, together with the isolation plate 8, coin-cell battery 3 and the electronic module 4 with the microprocessor are based on bottom housing 5. The bottom housing 5 is mounted on a drug dispenser that puts mechanical resistance resulting from the construction of the drug release valve in the dispenser B. This form of device construction implies that the kinetic force of the pressure acting on the dispensing valve in the drug dispenser B is also the kinetic force of the pressure piezoelectric transducer 2.

Operating Principle of the Piezoelectric Transducer in Example 1

The transmission of the kinetic force of the pressure from the activator 1 of the drug release measurement sensor—piezoelectric transducer—which is the top cover to the piezoelectric transducer 2 causes mechanical stress of the piezoelectric transducer 2. Mechanical stress of the piezoelectric transducer 2 causes the appearance of electric charges on its surface. Thus, the piezoelectric transducer 2 converts the kinetic force of the pressure into electricity, which is then transmitted via wires to the microprocessor, which is located in the electronic module 4. The electronic module 4 and the microprocessor are powered by coin-cell battery 3.

Measuring Pressure by a Piezoelectric Transducer in the Cap in Example 1

As shown in FIG. 5, the action of the kinetic force of the pressure Fn1 on the upper cover 1, which is the activator of the piezoelectric transducer made of elastic material, i.e. an elastomer, which can transform a part of the kinetic force of the pressure Fn1 into the elastic force Fs1, causes the transfer of the kinetic force Fn2 to the piezoelectric transducer 2. The kinetic force of the pressure Fn2 acting on the piezoelectric transducer 2 through the mechanical voltage of the piezoelectric transducer 2 generates electric charges of electrical voltage, which are then transmitted via wires to the microprocessor, which is located in the electronic module 4.

The microprocessor in the electronic module 4 measures the electrical voltage generated by the piezoelectric transducer 2. As shown in FIG. 6, the microprocessor compares the measured electrical voltage with the value of the electrical voltage threshold Up programmed in the microprocessor. The electrical voltage threshold Up programmed in the microprocessor may result from the threshold of force Fp required for the correct use of the drug as a result of the mechanical resistance of the dispensing valve in the drug dispenser. If the value of the measured electrical voltage is greater than or equal to the value of programmed electrical voltage threshold Up, the microprocessor records the correct use of the drug, while if the value of the measured electrical voltage is less than the value of programmed electrical voltage threshold Up, the microprocessor records the attempt to use the drug—incorrect use of the drug. Registered correct drug use and drug use attempts can be saved to the microprocessor and can be sent to external devices (e.g. computer, telephone or other electronic device) wirelessly.

Sound Signaling by a Piezoelectric Transducer in the Cap in Example 1

The electronic module 4 also has the ability to generate electrical impulses and transmit them via wires to the piezoelectric transducer 2. Electrical impulses transmitted to the piezoelectric transducer cause deformation of the piezoelectric material in the piezoelectric transducer, which causes the movement of the metal plate—membrane, resulting in the creation of sound waves in the air. In order for the sounds to get out of the cap housing, the upper casing 1 has an hole 7. The sound produced by the piezoelectric transducer 2 can be used to signal various events associated with the use of the drug. The microprocessor may have programmed various events that require audible signalling, including signalling of correct or incorrect use of the inhaler, signalling of individual stages when attempting to use the inhaler, and signalling of events related to the device status. For this purpose, it can use electrical impulses generated by the kinetic force of pressure Fn2 acting on the piezoelectric transducer 2 or by the coin-cell battery 3 located in the device.

EXAMPLE 2

Elements of the Invention in Example 2

As shown in FIG. 7, in another embodiment of the invention, the cap includes an activator 1 of the drug release measurement sensor—a piezoelectric transducer sensor—which is the top cover with a flange 1a and bulge 1b, coin-cell battery 3, piezoelectric transducer 2, electronic module 4 containing microprocessor, isolation plate 8, bottom housing 5 with socket 5a together with mounting on the dispenser, resonance chamber 6, hole 7 in the casing enabling the sound from the piezoelectric transducer to spread beyond the cap, reflection spring 9. Upper casing to act as a drug use sensor—piezoelectric transducer—it must be made of rigid plastic in the shape of a round disc, with a bulge directed inwards in the center of the top cover and a specific flange 1a, which fits into the socket 5a, enabling it to mount positioning on the bottom housing 5.

Construction and Operation of the Invention in Example 2

As shown in FIG. 7, the cap is mounted on the drug dispenser, e.g. on an inhaler. In this example, the drug release measurement sensor activator 1—piezoelectric transducer—being the top cover is made of plastic that does not bend, however it has a specific collar 1a that fits into the socket 5a in the lower part of the bottom housing 5 and the bulge 1b. The flange 1a and the socket 5a fit in such a way that minimal vertical movement of the top cover is possible. While taking the drug, the user acts with a kinetic force on the activator, which relies on the reflecting spring, bending it, then by bulging 1b, transfers this force down to the piezoelectric transducer 2, which rests on the isolation plate 8, then on the electronic module 4 with microprocessor, further on the coin-cell battery 3, which rests on the bottom of the bottom housing 5. In the dispenser base state, piezoelectric transducer 2 is not in close contact with the bulge of activator 1b—it does not stick to the activator of piezoelectric transducer, but between the position of piezoelectric transducer 2, and the bulge 1b of the activator is a distance equal to the mobility of the collar 1a, when the drug is released, in relation to the socket 5a.

When the inhaler is not used, a free space is created between the transducer 2 and the bulge 1b of the activator, which is the top cover in the embodiment, which creates a resonance chamber 6. At the moment of pressure, the activator 1 moves the pressure through movement—the kinetic force that causes movement—on the reflection spring 9, which is able to deform under the influence of a force applied during pressure on it, at its maximum deflection resulting from the mobility of the collar 1a in relation to the socket 5a, it allows the pressure force to be transferred to the bulge 1b in the activator by piezoelectric transducer 2, including thereby deforming the piezoelectric transducer 2. Deformation of the piezoelectric transducer absorbs insignificant amount of pressure kinetic force for the invention, so it can be assumed that the kinetic force of the pressure acting on the piezoelectric transducer and the kinetic force of the pressure transmitted to subsequent elements of the device Equipment kinetic pressure is the force of the same value. Then, the piezoelectric transducer 2 rests on an isolation plate 8, then on the electronic module 4 containing the microprocessor, then on the coin-cell battery 3 which rests on the bottom housing 5. The bottom housing 5 is mounted on a dispenser with a drug that creates mechanical resistance resulting from the construction of the release valve drug in the B dispenser. This form of device construction implies that the kinetic force of pressure acting on the dispensing valve in the B dispenser with the drug is also the kinetic force of pressure acting on the piezoelectric transducer 2.

Operating Principle of the Piezoelectric Transducer in Example 2

Transmission of the kinetic force of the pressure by bulging the activator 1b to the piezoelectric transducer 2 causes mechanical stress of the piezoelectric transducer 2. Mechanical stress of the piezoelectric transducer 2 causes electric charges to appear on its surface. Thus, the piezoelectric transducer 2 converts the kinetic force of the pressure into electricity, which is then transmitted via wires to the microprocessor, which is located in the electronic module 4. The electronic module 4 with the microprocessor is powered by a coin-cell battery 3.

Measuring Pressure by a Piezoelectric Transducer in the Cap in Example 2

As shown in FIG. 8, the kinetic force of the pressure Fn1 activator 1 causes the kinetic force 2 of the pressure Fn3 to be transferred to the piezoelectric transducer 2. The kinetic force of the Fn3 pressure acting on the piezoelectric transducer 2 through the mechanical voltage of the piezoelectric transducer 2 generates electric charges of electrical voltage force, which are then transferred via wires to the microprocessor, which is located in the electronic module 4.

The microprocessor in the electronic module 4 measures the electrical voltage generated by the piezoelectric transducer 2. As shown in FIG. 6, the microprocessor compares the measured electrical voltage with the electrical voltage threshold Up programmed in the microprocessor. The electrical voltage threshold Up programmed in the microprocessor may result from the threshold of force Fp required for the correct use of the drug as a result of the mechanical resistance of the dispensing valve in the drug dispenser. If the value of electrical voltage is greater than or equal to the programmed electrical voltage threshold Up, the microprocessor records the correct use of the drug, while if the value of measured electrical voltage is smaller than the value of programmed electrical voltage threshold Up, the microprocessor records the attempt to use the drug—incorrect use of the drug. Registered correct drug use and drug use attempts can be saved to the microprocessor and can be sent to external devices (e.g. computer, telephone or other electronic device) wirelessly.

The electronic module 4 also has the ability to generate electrical impulses and transmit them via wires to the piezoelectric transducer 2. Electrical impulses transmitted to the piezoelectric transducer cause deformation of the piezoelectric material in the piezoelectric transducer, which causes the movement of the metal plate—membrane, resulting in the creation of sound waves in the air. In order for the sounds to get out of the cap housing, the bottom housing 5 has an hole 7. The sound produced by the piezoelectric transducer 2 can be used to signal various events associated with the use of the drug. The microprocessor may have programmed various events that require audible signaling, including signaling of correct or incorrect use of the inhaler, signaling of individual stages when attempting to use the inhaler, and signaling of events related to the device status. For this purpose, it can use electrical impulses generated by the kinetic force of pressure Fn3 acting on the piezoelectric transducer 2 or by the coin-cell battery 3 located in the device.

The invention claimed is:

1. A device for monitoring a drug intake from a dispenser, the device having a form of a dispenser cap and comprising:
    a measurement sensor for measuring the drug intake from the dispenser wherein the measurement sensor is a piezoelectric transducer,
    a microprocessor connected with the measurement sensor,
    an activator for the measurement sensor contactable with the measurement sensor,
    wherein the measurement sensor is located within the dispenser cap such that the force used to press the dispenser cap is transferred as a kinetic force from the activator to the measurement sensor that measures the transferred kinetic force;
    wherein the activator forms an upper cover of a housing of the dispenser cap, wherein the upper cover is located above the measurement sensor and wherein the device further comprises a reflection spring such that a pressure applied on the upper cover causes a pressure on the reflection spring, wherein a maximum deflection of the reflection spring causes a contact of the upper cover with the piezoelectric transducer, thereby causing the force of the pressure to be transferred to the measurement sensor.

2. The device according to claim 1, wherein the activator and the measurement sensor are located coaxially with the cap.

3. The device according to claim 1, wherein the measurement sensor is located between the activator and a lower housing mounted on the dispenser.

4. The device according to claim 1, wherein the activator comprises elastic elements.

5. The device according to claim 1, wherein the upper cover is located above the measurement sensor, thereby forming a resonance chamber and the activator comprises an element made of at least one of: an elastomer material, a plastic material, a metal material, polymer material, a ceramic material and a composite material, and wherein a pressure applied onto the activator causes a contact with the measurement sensor, thereby causing the force of the pressure to be transferred to the measurement sensor.

6. The device according to claim 1, the reflection spring, in a base position, allows formation of the resonance chamber between the measurement sensor and the activator.

7. The device according to claim 1, wherein a resonance chamber is formed between the activator and the measurement sensor in a base state without a pressure applied on the dispenser cap.

8. A device for monitoring a drug intake from a dispenser, the device having a form of a dispenser cap and comprising:
    a measurement sensor for measuring the drug intake from the dispenser wherein the measurement sensor is a piezoelectric transducer;
    a microprocessor connected with the measurement sensor;
    an activator for the measurement sensor contactable with the measurement sensor, wherein the measurement sensor is located within the dispenser cap such that the force used to press the dispenser cap is transferred as a kinetic force from the activator to the measurement sensor that measures the transferred kinetic force; and
    an acoustic signal generator that functions as the measurement sensor.

9. The device according to claim 8, comprising a resonant chamber and an opening made in the activator such that a sound from the measurement sensor spreads beyond the dispenser cap.

10. A device for monitoring a drug intake from a dispenser, the device having a form of a dispenser cap and comprising:
    a measurement sensor for measuring the drug intake from the dispenser wherein the measurement sensor is a piezoelectric transducer;
    a microprocessor connected with the measurement sensor;
    an activator for the measurement sensor contactable with the measurement sensor, wherein the measurement sensor is located within the dispenser cap such that the force used to press the dispenser cap is transferred as a kinetic force from the activator to the measurement sensor that measures the transferred kinetic force; and
    wherein the activator is made of a flexible material that can bend into a resonance chamber area.

11. A method of monitoring a drug intake from a dispenser, the method comprising:
    providing a dispenser cap with a measurement sensor to measure a drug release while pressure is applied on the dispenser cap, wherein the measurement sensor has a form of a piezoelectric transducer connected to an electronic module with a microprocessor, wherein the measurement sensor is located in the dispenser cap coaxially with an activator of the measurement sensor,
    when a pressure is applied on the cap during activating the drug release from the dispenser, transferring a kinetic force of pressing the dispenser cap to the measurement sensor by movement of the activator;
    generating an electric voltage in the measurement sensor resulting from the kinetic force acting on the measurement sensor, transmitting the electric voltage to the electronic module,
at the microprocessor, using an algorithm to convert the electric voltage into a numerical value and comparing the numerical value with a programmed numerical value that corresponds to a threshold value of the kinetic force and registering the numerical value, transferring the kinetic force applied to the measuring sensor to further elements of the device up to a lower housing mounted on the dispenser, then on the drug dispenser and finally releasing the drug;
in response to detecting that numerical value of the kinetic force of the pressure exceeds a minimum threshold of the numeric value of the kinetic force programmed in the electronic module, recording this situation by the electronic module as a correct dosage of the drug,
and in response to detecting that the numerical value of the kinetic force of the pressure does not exceed the minimum threshold of the numeric value of the kinetic force programmed in the electronic module, recording this situation by the electronic module as an attempt to dose the drug.

12. A method of generating sound signals for communication with a user of a dispenser, the method comprising:
providing a dispenser cap with a measurement sensor to measure a drug release while pressure is applied on the dispenser cap, wherein the measurement sensor has a form of a piezoelectric transducer connected to an electronic module with a microprocessor, and wherein the measurement sensor is located in a dispenser cap adjacently to a resonance chamber having an opening that allows sound signals to pass outside the cap, wherein the microprocessor is powered by a coin-cell battery;
generating sound signals as a result of one of events programmed in the microprocessor by sending an electric pulse to the measurement sensor thereby causing a metal plate of the piezoelectric transducer to move and consequently generate sound waves in air that travel outside the dispenser cap via the resonance chamber with the opening.

* * * * *